United States Patent [19]
Oviatt

[11] Patent Number: 5,927,279
[45] Date of Patent: Jul. 27, 1999

[54] EYE PATCH

[75] Inventor: Lorna Oviatt, Edson, Canada

[73] Assignee: William Oviatt, Spruce Grove, Canada

[21] Appl. No.: 08/820,265

[22] Filed: Mar. 18, 1997

[30] Foreign Application Priority Data

Mar. 19, 1996 [CA] Canada ................................. 2172100

[51] Int. Cl.⁶ .................................................. A61F 11/00
[52] U.S. Cl. .................................................. 128/857; 2/13
[58] Field of Search .................................. 128/846, 857, 128/858; 2/9, 13, 15

[56] References Cited

U.S. PATENT DOCUMENTS

| | | | |
|---|---|---|---|
| 4,726,075 | 2/1988 | Hinrichs | 2/13 |
| 4,751,746 | 6/1988 | Rustin | 2/13 |
| 4,843,643 | 7/1989 | Parissenti | 128/857 |
| 4,862,902 | 9/1989 | Goffman | 128/858 |
| 5,402,189 | 3/1995 | Gill | 2/13 |

*Primary Examiner*—Michael A. Brown
*Attorney, Agent, or Firm*—Davis and Bujold

[57] ABSTRACT

An eye patch including a substantially planar flexible elongate body having a first end and a second end. At least one transverse slot extends through the body adjacent each of the first end and the second end. The body is mounted onto a pair of eye glasses by extending an arm through one slot and a nose pad through the other slot. When in position the body extends across a lens receiving socket to block vision through a lens and extends substantially along the arm to block peripheral vision.

3 Claims, 4 Drawing Sheets

EYE PATCH

FIELD OF THE INVENTION

The present invention relates to an eye patch.

BACKGROUND OF THE INVENTION

Every sighted person has one eye that is dominant to a greater or lesser degree. An overwhelming dominance of one eye, however, is viewed as being harmful as it can, in extreme cases, lead to a loss of sight in the weaker eye. A tendency toward total dependency upon the dominant eye is present with such conditions as crossed-eyes, diverging eyes or eye muscle imbalances. In young children, if one eye shows an overwhelming dominance, an eye patch is placed over the dominant eye. This treatment is intended to force reliance upon the weaker eye. It has been demonstrated that this treatment will, over time, result in the strengthening of the weaker eye. Normally eye glasses are prescribed, as corrective lenses have been demonstrated to accelerate the rehabilitation of the weaker eye.

The dominance of the dominant eye is so complete, that rehabilitation of the weaker eye is retarded if the child can use his or her peripheral vision to see out of the dominant eye. For this reason the sight lines of the dominant eye must be completely blocked. In order to cover the dominant eye, an eye patch is used. In order to ensure the sight lines are completely blocked by the eye patch, the eye patch is secured across the dominant eye with adhesive. This manner of attaching the eye patch has numerous disadvantages. The adhesive invariably adheres to the child's eye brows, resulting in the child experiencing discomfort when the eye patch is removed. The eye patch can be uncomfortable, especially when the child becomes over heated during play and perspires.

SUMMARY OF THE INVENTION

What is required is a form of eye patch that does not require adhesive.

According to one aspect of the present invention there is provided an eye patch including a substantially planar flexible elongate body having a first end and a second end. At least one transverse opening extends through the body adjacent each of the first end and the second end.

It is preferred that the body be constructed out of a soft fabric which can be washed when soiled by dirt or perspiration.

According to another aspect of the present invention there is provided an eye patch substantially as described above in combination with a pair of eye glasses. A pair of eye glasses is provided including a frame with a first lens receiving socket and a second lens receiving socket. A lens is positioned in the second lens receiving socket. Each of the first lens receiving socket and the second lens receiving socket has an interior edge and an exterior edge. The interior edges of the first lens receiving socket and the second lens receiving socket are connected by a bridge. A first nose pad is secured to the interior edge of the first lens receiving socket. A second nose pad is secured to the interior edge of the second lens receiving socket. A first arm is secured perpendicularly to the exterior edge of the first lens receiving socket. A second arm is secured to the exterior edge of the second lens receiving socket. The eye patch, as described above, includes a substantially planar flexible elongate body having a first end and a second end. A first transverse opening extends through the body adjacent the first end. A second transverse opening extends through the body adjacent the second end. The eye patch is placed onto the eye glasses by extending the first arm through the second opening and extending the first nose pad through the first opening. The body extends across the first lens receiving socket to block vision through the first lens receiving socket and extends substantially along the first arm to block peripheral vision.

BRIEF DESCRIPTION OF THE DRAWINGS

These and other features of the invention will become more apparent from the following description in which reference is made to the appended drawings, wherein.

DETAILED DESCRIPTION OF THE PREFERRED EMBODIMENT

Figure 1:
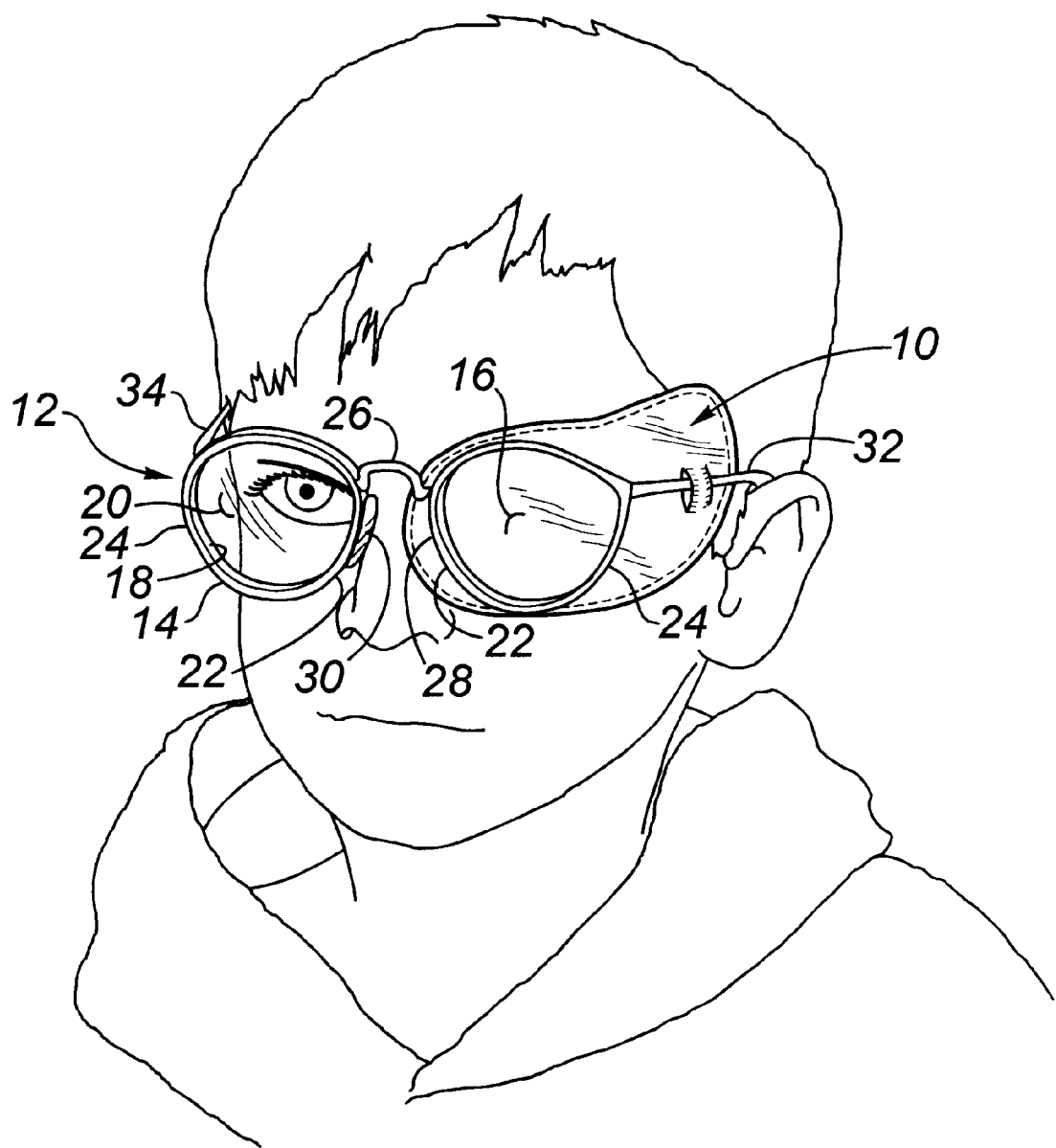
FIG. 1 is a perspective view of an eye patch constructed in accordance with the teachings of the present invention on a pair of eye glasses.

The preferred embodiment, an eye patch generally identified by reference numeral 10, will now be described with reference to FIGS. 1 through 6.

Referring to FIG. 1, eye patch 10 is expressly designed for mounting onto a pair of eye glasses 12. Eye glasses 12 include a frame 14 with a first lens receiving socket 16 and a second lens receiving socket 18. A lens 20 is positioned in second lens receiving socket 18. Each of first lens receiving socket 16 and second lens receiving socket 18 have an interior edge 22 and an exterior edge 24. Interior edges 22 of first lens receiving socket 16 and second lens receiving socket 18 are connected by a bridge 26. A first nose pad 28 is secured to interior edge 22 of first lens receiving socket 16. A second nose pad 30 is secured to interior edge 22 of second lens receiving socket 16. A first arm 32 is secured perpendicularly to exterior edge 24 of first Lens receiving socket 16. A second arm 34 is secured to exterior edge 24 of second lens receiving socket 18.

Figure 2:
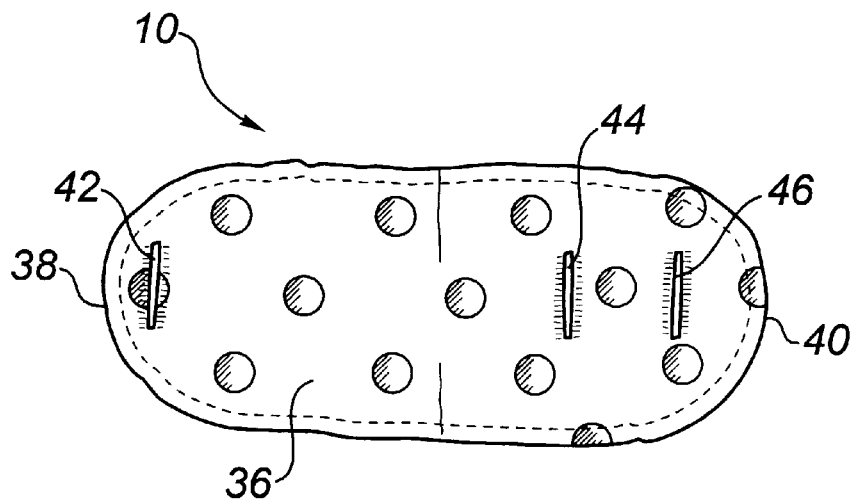
FIG. 2 is a top plan view of an eye patch constructed in accordance with the teachings of the present invention.

Referring to FIG. 2, eye patch 10 includes a substantially planar soft flexible elongate fabric body 36 having a first end 38 and a second end 40. A first transverse slotted opening 42 extends through the body adjacent first end 38. A second transverse slotted opening 44 and a third transverse slotted opening 46 positioned in parallel spaced relation extend through body 36 adjacent second end 40.

Figure 3:
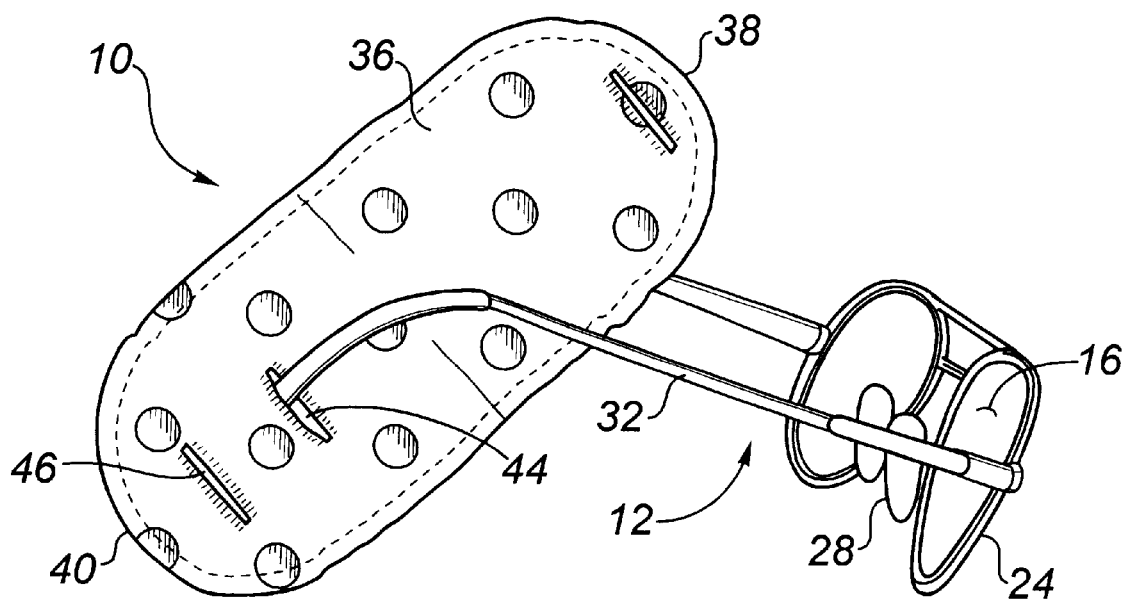
FIG. 3 is a perspective view illustrating a step in placing the eye patch illustrated in FIG. 2 onto a pair of eye glasses.
Figure 4:
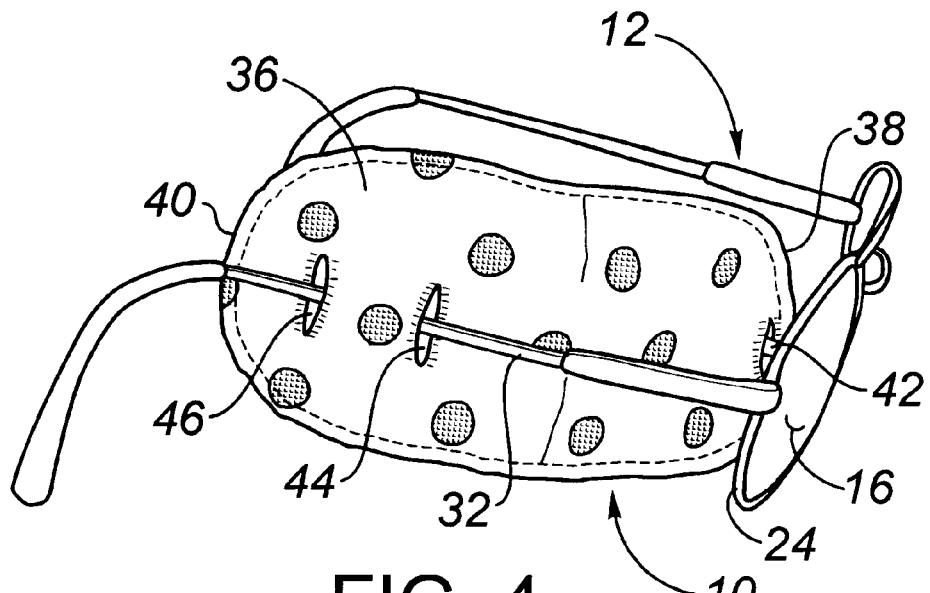
FIG. 4 is a side elevation view of the eye patch illustrated in FIG. 2 secured to a pair of eye glasses.
Figure 5:
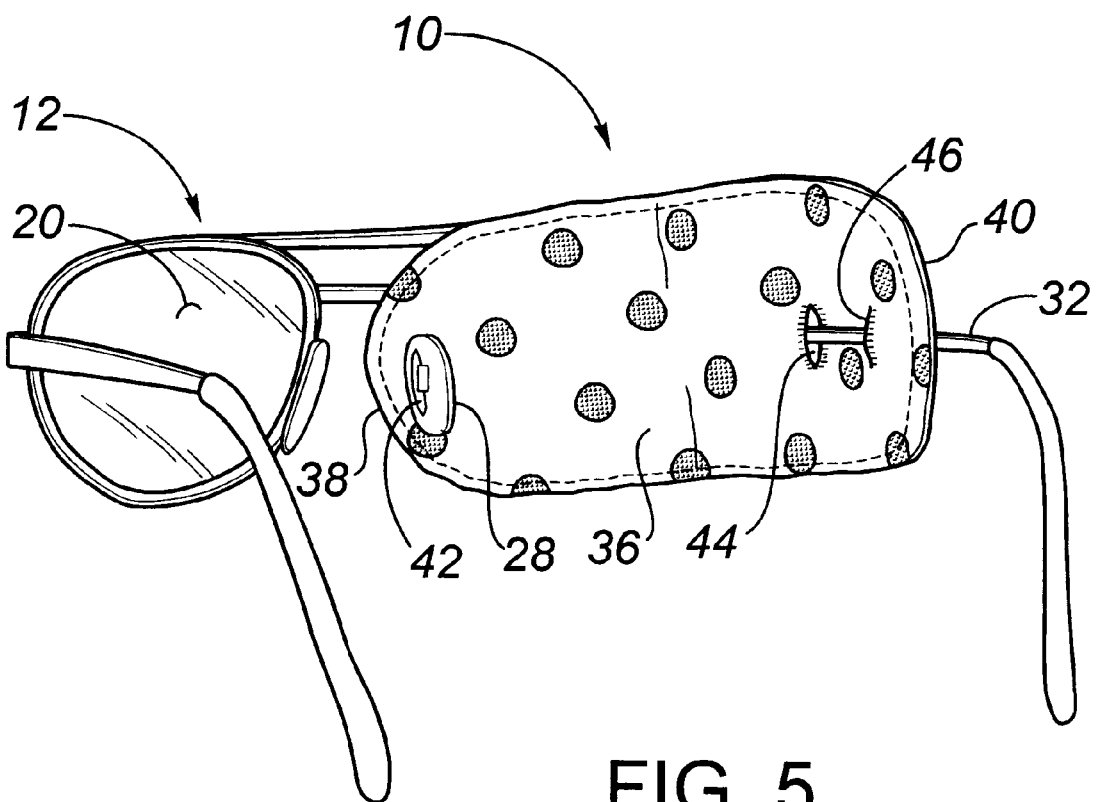
FIG. 5 is a rear elevation view of the eye patch illustrated in FIG. 2 secured to a pair of eye glasses.
Figure 6:
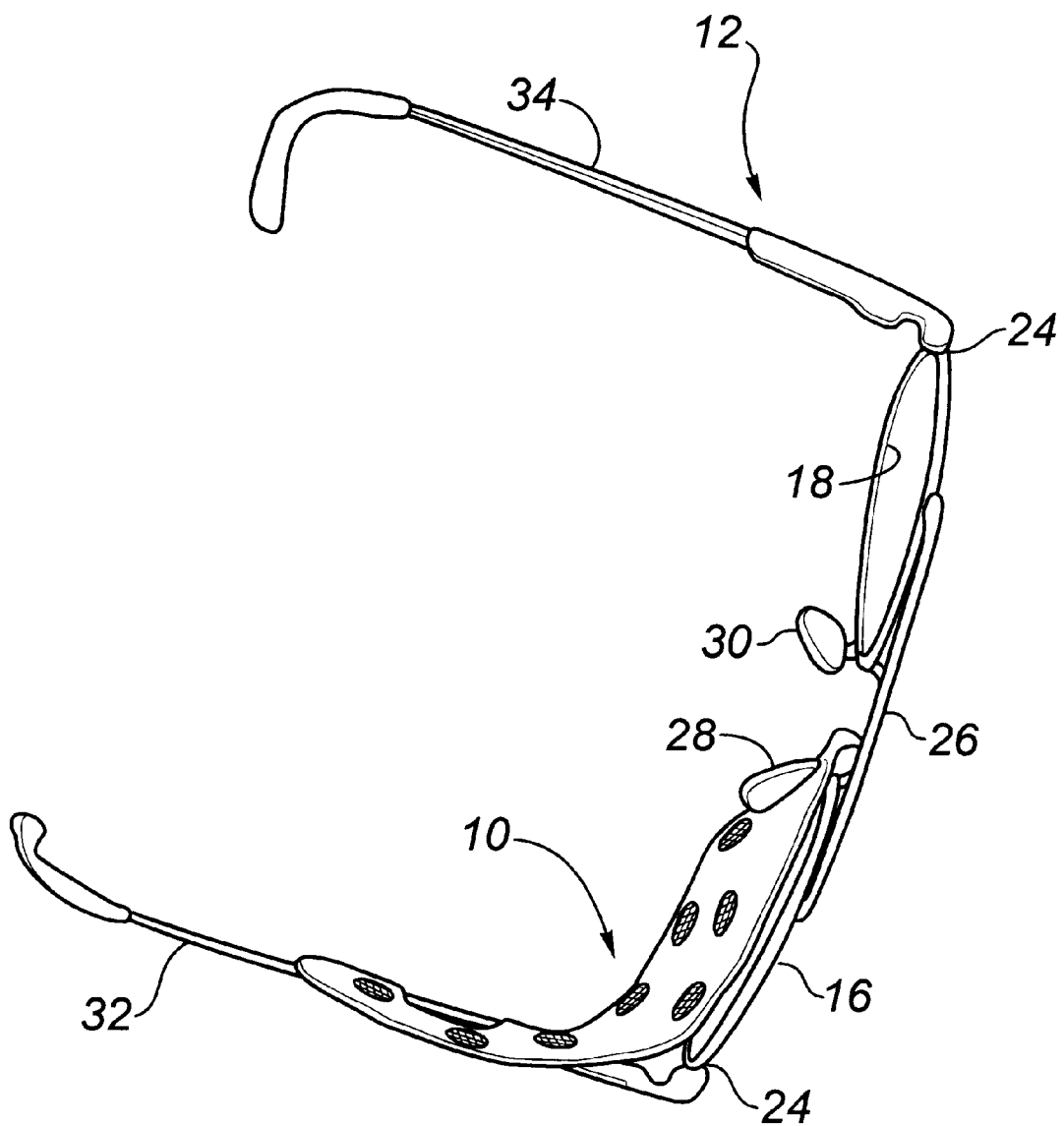
FIG. 6 is a top plan view of the eye patch illustrated in FIG. 2 secured to a pair of eye glasses.

Referring to FIG. 3, eye patch 10 being placed onto eye glasses 12 by extending first arm 32 through second slot 44 and third slot 46. Referring to FIGS. 4 through 6, body 36 is then pulled around to permit first nose pad 28 to be extended through first slot 42. Body 36 extends across first lens receiving socket 16 to block vision through first lens receiving socket 16 and extends substantially along first arm 32 to block peripheral vision.

It will be apparent to one skilled in the art that modifications may be made to the illustrated embodiment without departing from the spirit and scope of the invention as hereinafter defined in the Claims.

The embodiments of the invention in which an exclusive property or privilage is claimed are defined as follows:

1. In combination:
   a pair of eye glasses including a frame with a first lens receiving socket and a second lens receiving socket, a lens positioned in the second lens receiving socket, each of the first lens receiving socket and the second lens receiving socket having an interior edge and an exterior edge, the interior edges of the first lens receiving socket and the second lens receiving socket being connected by a bridge, a first nose pad being secured to the interior edge of the first lens receiving socket and a second nose pad being secured to the interior edge of the second lens receiving socket, a first arm being secured to the exterior edge of the first lens receiving socket and a second arm being secured to the exterior edge of the second lens receiving socket;
   an eye patch including a substantially planar flexible elongate body having a first end and a second end, a first transverse opening extending through the body adjacent the first end and a second transverse opening extending through the body adjacent the second end; and
   the eye patch being placed onto the eye glasses by extending the first arm through the second opening and extending the first nose pad through the first opening, such that the body extends completely across the first lens receiving socket to block vision through the first lens receiving socket and extends substantially along the first arm to block peripheral vision.

2. In combination:
   a pair of eye glasses including a frame with a first lens receiving socket and a second lens receiving socket, a lens positioned in the second lens receiving socket, each of the first lens receiving socket and the second lens receiving socket having an interior edge and an exterior edge, the interior edges of the first lens receiving socket and the second lens receiving socket being connected by a bridge, a first nose pad being secured to the interior edge of the first lens receiving socket and a second nose pad being secured to the interior edge of the second lens receiving socket, a first arm being secured to the exterior edge of the first lens receiving socket and a second arm being secured to the exterior edge of the second lens receiving socket;
   an eye patch including a substantially planar soft flexible elongate fabric body having a first end and a second end, a first transverse slot extending through the body adjacent the first end and a second transverse slot and a third transverse slot in parallel spaced relation extending through the body adjacent the second end; and
   the eye patch being placed onto the eye glasses by extending the first arm through the second slot and the third slot and extending the first nose pad through the first slot, such that the body extends completely across the first lens receiving socket to block vision through the first lens receiving socket and extends substantially along the first arm to block peripheral vision.

3. In combination:
   a pair of eye glasses including a frame with a first lens receiving socket and a second lens receiving socket, a lens positioned in the second lens receiving socket, each of the first lens receiving socket and the second lens receiving socket having an interior edge and an exterior edge, the interior edges of the first lens receiving socket and the second lens receiving socket being connected by a bridge, a first nose pad being secured to the interior edge of the first lens receiving socket and a second nose pad being secured to the interior edge of the second lens receiving socket, a first arm being secured to the exterior edge of the first lens receiving socket and a second arm being secured to the exterior edge of the second lens receiving socket;
   an eye patch including a substantially planar flexible elongate body having means for attaching to a frame of a pair of eye glasses; and
   the eye patch being placed onto the eye glasses with the body extending completely across the first lens receiving socket and a first end of said eye patch engaging with said first nose pad via the means for attaching to block vision through the first lens receiving socket and also extending substantially along the first arm to block peripheral vision.

* * * * *